(12) United States Patent
Palaniappan et al.

(10) Patent No.: US 7,914,983 B2
(45) Date of Patent: Mar. 29, 2011

(54) DETECTION METHOD FOR GENE EXPRESSION

(75) Inventors: Chockalingam Palaniappan, Eugene, OR (US); Carl W. Fuller, Berkeley Heights, NJ (US); John R. Nelson, Clifton Park, NY (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 482 days.

(21) Appl. No.: 11/427,395

(22) Filed: Jun. 29, 2006

(65) Prior Publication Data

US 2007/0003953 A1 Jan. 4, 2007

Related U.S. Application Data

(60) Provisional application No. 60/695,549, filed on Jun. 30, 2005.

(51) Int. Cl.
*C12Q 1/68* (2006.01)
*C12P 19/34* (2006.01)
*C12M 1/34* (2006.01)
*C07H 21/04* (2006.01)

(52) U.S. Cl. ....... 435/6; 435/91.1; 435/91.2; 435/287.2; 536/23.1; 536/24.31; 536/24.33

(58) Field of Classification Search .................. None
See application file for complete search history.

(56) References Cited

U.S. PATENT DOCUMENTS

| | | | |
|---|---|---|---|
| 6,004,755 A | 12/1999 | Wang | |
| 2002/0119455 A1* | 8/2002 | Chan | 435/6 |
| 2006/0286570 A1* | 12/2006 | Rowlen et al. | 435/6 |
| 2007/0009954 A1* | 1/2007 | Wang et al. | 435/6 |
| 2007/0031829 A1* | 2/2007 | Yasuno et al. | 435/6 |
| 2007/0042400 A1* | 2/2007 | Choi et al. | 435/6 |
| 2007/0042419 A1* | 2/2007 | Barany et al. | 435/6 |

FOREIGN PATENT DOCUMENTS

| WO | WO93/24655 | 12/1993 |
|---|---|---|
| WO | WO2004/052907 | 6/2004 |
| WO | WO2004/096997 | 11/2004 |

OTHER PUBLICATIONS

Zhang et al., Bioinformatics, vol. 19, No. 1, 2003, pp. 14-21.*
Schena, M., et al., "Parallel Human Genome Analysis: Microarray-Based Expression Monitoring of 1000 Genes", Proceedings of the National Academy of Sciences of USA, National Academy of Sciences of USA, Washington, DC, US, vol. 93, No. 20, Oct. 1996, p. 10614-10619.
Watakabe, A., et al., "Similarity and Variation in Gene Expression Among Human Cerebral Cortical Subregions Revealed by DNA Macroarrays: Technical Consideration of RNA Expression Profiling from Postmortem Samples", Molecular Brain Research, vol. 88, No. 1-2, Mar. 2001, p. 74-82.

* cited by examiner

*Primary Examiner* — Bradley L Sisson
(74) *Attorney, Agent, or Firm* — Yonggang Ji

(57) ABSTRACT

Provided is a novel approach for generating oligonucleotide probes and the use of these probes in gene expression profiling, by hybridization to test oligonucleotides on arrays or beads. This approach involves labeling of the complement oligonucleotide probes using a mixture of dye or hapten labeled-ddNTPs in solution. The labeled oligonucleotide probes are then used to hybridize to the test oligonucleotides on the solid support. Success in hybridization is monitored by associated signal on the solid support. This approach greatly reduces hybridization time, due to the simplification of the probe content. It is especially useful when analyzing a small number of genes, such as a signature set of genes for a disease or condition.

19 Claims, 3 Drawing Sheets

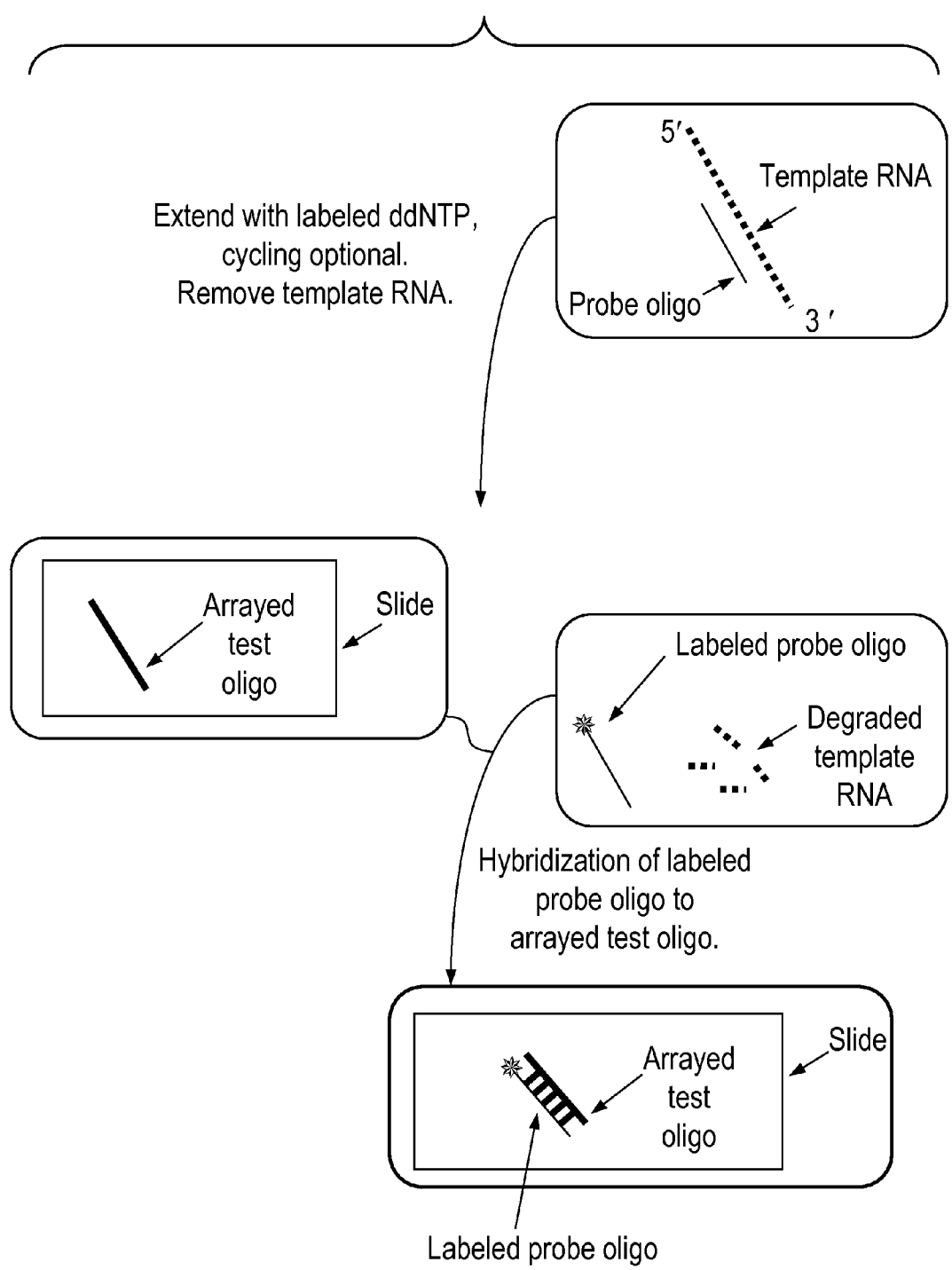

DETECTION METHOD FOR GENE EXPRESSION

CROSS-REFERENCE TO RELATED APPLICATIONS

This application claims priority to United States provisional patent application No. 60/695,549 filed Jun. 30, 2005; the disclosures of which are incorporated herein by reference in their entireties.

FIELD OF THE INVENTION

The present invention relates to a method for detection and quantification of gene expression, and to the use of this method in gene expression profiling and disease diagnostics. More specifically, the invention relates to the generation of labeled oligonucleotide probes and the use of these probes in bead or array based gene expression analysis.

BACKGROUND OF THE INVENTION

Oligonucleotide arrays for gene expression are increasingly becoming popular. The ability to produce mass arrays either by spotting pre-synthesized oligonucleotides or by in situ synthesis such as photolithographic means reliably and to perform gene expression studies reproducibly using such arrays has generated great deal of enthusiasm in the microarray research community. Increasingly, gene expression profiling is becoming a mainstream tool for molecular diagnosis of genomic disorders such as cancer. Oligonucleotide arrays also overcome some practical difficulties encountered with cumbersome process of generating CDNA arrays such as a prerequisite for mRNA source, massive parallel RT-PCR reactions, cloning and sequence verifications.

There are several different labeling protocols that researchers employ in studying gene expression on the cDNA arrays, but when applied to oligo arrays they do not work to satisfaction. Listed below are some common methods researchers use to generate probes in a microarray gene expression experiment. 1) Labeling during first strand cDNA synthesis using either wild type or modified reverse transcriptase (either using oligo dT primers and/or random primers). 2) "Modified Eberwine method", a strategy that relies on generating RNA probes by labeling during RNA synthesis and has the advantage of RNA amplification. The strategy is cumbersome and requires multiple steps that require the conversion of the RNA into DNA with a suitable promoter for enabling amplification. Further the process requires at least 4 different enzymes, ranging from RT, RNA polymerase, DNA ligase, RNase H and other additives. Additionally, the exponential nature of amplification has the potential to skew the experimental results. 3) Labeling, post first strand synthesis by chemical coupling methods to allyl amino modified nucleotides is another accepted method. The advantages of these labeling methods for cDNA arrays is that a large proportion of the probes made are generally complementary to the extensive region (typically about 500 or more bases) on the arrays and therefore produce acceptable signal for studies.

However, the probes generated by the above methods will require a fragmentation step prior to use in oligo array experiments owing to limitations from hybridization thermodynamics of larger fragments of nucleic acid on solid support. Not only is the process laborious and cumbersome, fragmentation also renders a large proportion of labeled synthesized probes useless, because they lack the corresponding complementary region on the arrayed oligos. Hence, signal generated from such fragmented probes are likely to be a few orders of magnitude diminished, consequently resulting in difficulties with detection.

SUMMARY OF THE INVENTION

Here we provide a novel approach for generating oligonucleotide probes and the use of these probes in gene expression profiling, by hybridization to test oligonucleotides on solid support (arrays or beads). This approach involves labeling of the complement oligonucleotide probes (to those that are arrayed) using a mixture of dye or hapten labeled-ddNTPs and template in solution. The labeled oligonucleotide probes are then used to hybridize to the test oligonucleotides on the solid support, Success in hybridization is monitored by associated colors on the solid support. This approach greatly reduces the hybridization time, due to the simplification of the probe content. This is especially useful when analyzing a small number of genes, such as a signature set of genes for a disease or condition.

In accordance with one aspect of the present invention, there is provided a method for gene expression analysis, comprising first generating at least one labeled oligonucleotide probe by a method of (1) first algorithmically selecting a gene-specific target region sequence within each of at least one gene of interest; (2) then synthesizing anti-sense oligonucleotide probes that complement each of the selected target regions; (3) mixing the oligonucleotide probes with a source nucleic acid of interest to allow hybridization to occur; (4) adding a labeled dideoxy nucleotide to the 3' end of hybridized oligonucleotide probes by polymerase reaction (primer extension); and (5) recovering the oligonucleotide probes. The method further comprises providing test oligonucleotides on a solid support, which are complements in sequence to the probe oligonucleotides. Then the labeled oligonucleotide probes are hybridized with the test oligonucleotides. The labels are then detected, from the oligonucleotide probes hybridized to the test oligos on the solid support, to determine the expression level of each of the genes of interest.

In accordance with another aspect of the present invention, there is provided a method for gene expression analysis, comprising first generating at least one oligonucleotide probe by a method of (1) first algorithmically selecting a gene-specific target region sequence within each of at least one gene of interest; (2) then synthesizing a sense oligonucleotide probe identical in sequence to the target region of each gene of interest; (3) generating first strand cDNA from an RNA source; mixing the oligonucleotide probes with first strand cDNA to allow hybridization of the oligonucleotide probes with the first strand cDNA; (4) adding a labeled dideoxy nucleotide to the 3' end of hybridized oligonucleotide probes by polymerase reaction; and (5) recovering the labeled oligonucleotide probes. The method further comprises providing test oligonucleotides on a solid support, which are anti-sense to the gene sequence, and are complements in sequence to the probe oligonucleotides. Then the labeled oligonucleotide probes are hybridized with test oligonucleotides on the solid support, and the labels are detected to determine the expression level of each of the at least one gene of interest.

These methods for gene expression analysis could be applied to measure gene expression of the entire genome of an organism. For example, it is possible to design and synthesis a probe oligonucleotide for every gene of a genome, and produce labeled probes as described above. Expression level of every gene of a genome can be assessed by hybridizing these oligonucleotide probes to a microarray slide containing test oligonucleotides representing each gene of the organism.

Because labeling of the oligonucleotide probes is by primer extension, labeling of the probes can be achieved without first reverse transcribing the RNA to cDNA. Therefore these methods are well suited for gene expression profiling of bacterial and other prokaryotic RNA, as these RNA lacks poly A tail and is more cumbersome to be reverse transcribed. They are also well suited for profiling fragmented RNA, such as those from formalin fixed, paraffin embedded sample.

For measuring the gene expression level of human tissues/cells, between 30-100 thousand oligonucleotide probes are needed, and the same number of complement test oligonucleotides are needed as well, on a solid support. These methods for gene expression analysis could also be applied to measure gene expression of a subset of genes within a genome. This is especially useful as it could be used as a diagnostics method for a human disease or condition by identifying the expression pattern (signature) of a small signature set of genes.

In accordance with another aspect of the present invention, there is provided a method for comparative gene expression analysis, comprising (i) generating at least one oligonucleotide probe by first algorithmically selecting a gene-specific target region sequence within each of at least one gene of interest; than synthesizing anti-sense oligonucleotide probes that complement each of the selected target regions; (ii) labeling the at least one oligonucleotide probe with distinctive dyes or hapten for each of the source nucleic acid samples to be analyzed, by first mixing a portion of the oligonucleotide probes with one of the source nucleic acids to allow hybridization to occur; than adding a labeled dideoxy nucleotide to the 3' end of hybridized oligonucleotide probes by polymerase reaction; recovering the oligonucleotide probes; repeat step (ii) to label each additional source nucleic acid of interest with a distinctive label; and combining the labeled oligonucleotide probes. Then provide test oligonucleotides on a solid support, which are complements in sequence to the probe oligonucleotides. The labeled oligonucleotide probes are then hybridized with test oligonucleotides on the solid support. Each of the distinctive labels from the hybridized oligonucleotide probes are detected and quantified, providing the relative expression level for each gene from the source nucleic acid samples of interest.

In accordance with another aspect of the present invention, there is provided a method for comparative gene expression analysis, comprising (i) generating at least one oligonucleotide probe by first algorithmically selecting a gene-specific target region sequence within each of at least one gene of interest; and synthesizing a sense oligonucleotide probe identical in sequence to the target region of each gene of interest; (ii) labeling the at least one oligonucleotide probe with distinctive dyes or hapten for each of the source RNA sample to be analyzed, by (1) first generating first strand cDNA from one of the source RNA; (2) then mixing a portion of the oligonucleotide probes with first strand CDNA to allow hybridization of the oligonucleotide probes with the CDNA; (3) adding a labeled dideoxy nucleotide to the 3' end of hybridized oligonucleotide probes by polymerase reaction; (4) recovering the oligonucleotide probes; (5) repeating with a distinctive label for each additional source nucleic acid of interest; and (6) combining the distinctively labeled oligonucleotide probes. The method further includes providing test oligonucleotides on a solid support, which are complements in sequence to the probe oligonucleotides. The labeled oligonucleotide probes are then hybridized with test oligonucleotides on solid support. Each of the distinctive labels from the hybridized oligonucleotide probes on solid support is then detected, and the relative expression level for each gene is determined.

These methods for comparative gene expression analysis could be applied to compare gene expression of normal and disease samples, or any two samples of interest, and to identify expression profiles associated with a disease or condition. These results could provide diagnostic signatures for diseases or conditions that are associated with a change in the expression pattern of certain genes in a genome.

BRIEF DESCRIPTION OF THE DRAWINGS

FIG. 1 shows a schematic drawing according to one embodiment of the invention. FIG. 1A shows the embodiment as performed in a microarray-based format.

FIG. 2 illustrates an alternative probe labeling scheme for gene expression analysis according to the embodiments of this invention. Labeling of the oligonucleotide probe is performed with a dye or hapten labeled ddCTP and unlabeled dATP, dGTP and dTTP. Labeling of the oligonucleotide probe occurs when the C is incorporated.

DETAILED DESCRIPTION OF THE INVENTION

Figure 1B:
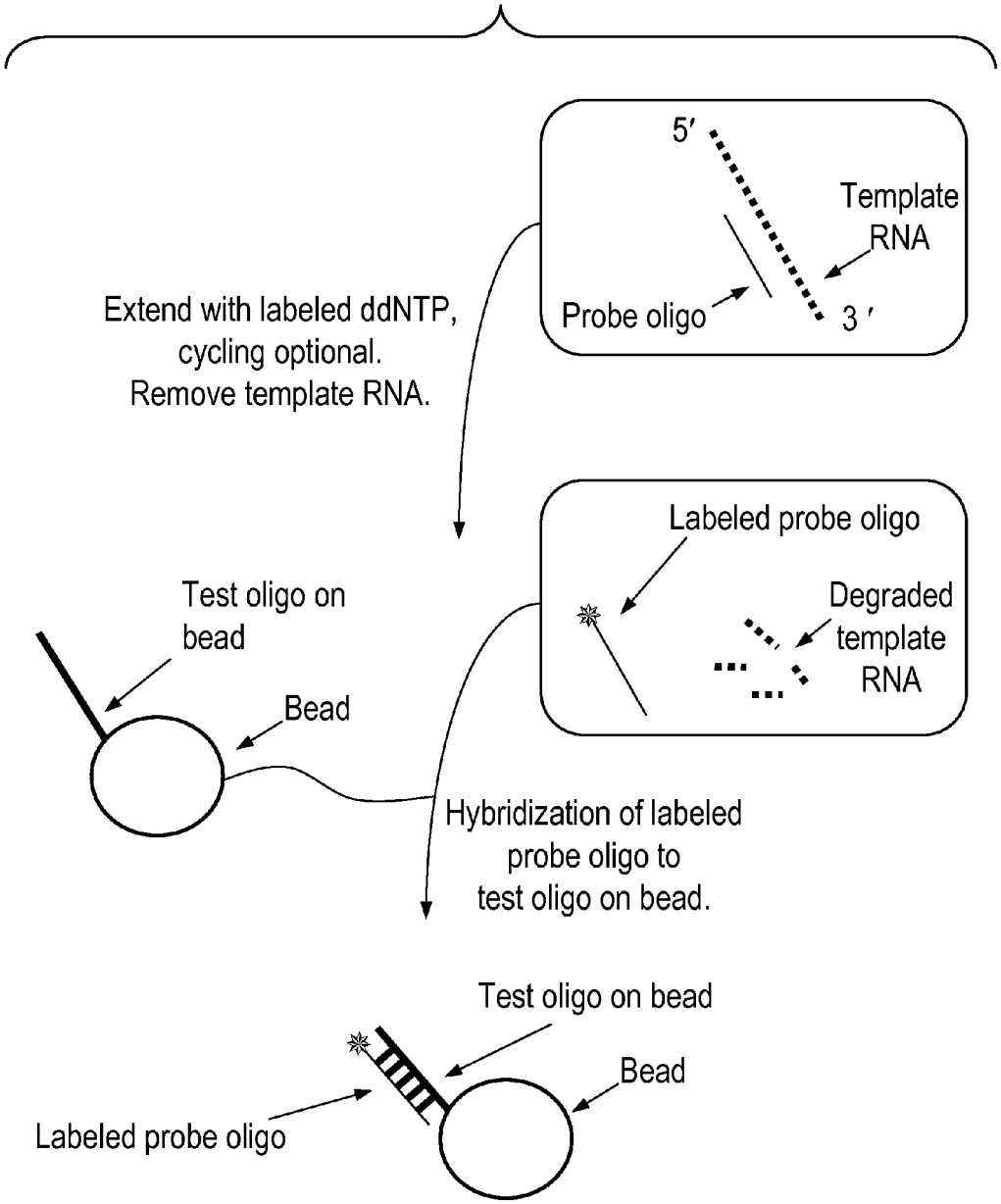
FIG. 1B shows the same embodiment, as performed in a bead-based format. The only difference is in the solid support being of different format.

We describe here methods for detection of gene expression using an approach that involves labeling, by a polymerase reaction, of the complement oligonucleotide probes (to those that are arrayed) with a mixture of dye or hapten labeled-ddNTPs and template nucleic acid in solution. This approach has a very important distinction from arrayed primer extension in that the oligonucleotide probes being labeled are in solution rather than on solid support. The extended oligonucleotide probes, which are labeled, are then used to hybridize to their partners (test oligonucleotides) on the solid support. The level of gene expression is measured by the presence and intensity of the color emitted from the label. The oligonucleotide probes are selected such that they only hybridize to the specific gene they derived from, both in the labeling step, and in the solid support hybridization step. Preferably, the oligonucleotide probes are from about 10 to about 100 nucleotides in length, more preferably from about 20 to about 60 nucleotides in length, or from about 20 to about 30 nucleotides in length. After labeling, the template nucleic acids are optionally degraded or separated from the labeled probes before the hybridization step.

Sometimes additional labeled probes are desired. In these instances, repeated denature, hybridization and polymerase reaction can be performed to achieve a linear increase of labeled probes. While labeled-ddNTP are often used for labeling, in some occasions it is advantageous to label the probes in the presence of a single labeled dideoxy nucleotide and three non-labeled deoxynucleotides, such as using a labeled ddCTP and non-labeled dATP, dGTP and dTTP. A number of polymerases can be used for the addition of labeled dideoxy nucleotide to the 3' end of the oligonucleotide probe, and the cycling of reaction. For example, DNA polymerase I (e.g. T7 DNA polymerase), or reverse transcriptase, can all be used to incorporate a labeled dideoxy nucleotide, to the 3' end of the oligonucleotide probe in a probe/RNA template complex. While the native enzymes are useful for these reactions, some engineered enzymes offer various advantageous, and could be used as well. When the template is a DNA template, most DNA polymerases can be used for the labeling reaction.

Dye or hapten-labeled nucleotides are well known in the art. Alternatively, the nucleotides can be labeled with radioisotopes as well. Detection methods for the dye or hapten labels are also well known. For the purpose of detection associated with the methods of the instant application, any dye/hapten label that is readily detectable can be used. Common labels such as Cynine dyes, IR dyes, Rhodamine dyes, Alexa dyes, and the biotin-streptavidin system are some examples. Since Cy3 and Cy5 dyes are the popular dyes employed in two-color differential gene expression studies, Cy3 or Cy5-ddNTPs are attractive candidates. These methods also offer the flexibility of easily integrating a $3^{rd}$ dye or a $4^{th}$ dye in the rhodamine class. Since labeling is limited to single nucleotide, rate of incorporation is not significantly limited even when structural changes to dye-nucleotide analogs are introduced, an issue which poses difficulty for other methods that rely on incorporation followed by extension.

While some labels are capable of providing a detectable signal directly (e.g. fluorescent dyes), some are through interaction with one or more additional members of a signal production system (e.g. haptens such as biotin-streptavidin). In some instances it is advantageous to use a hapten system. For a biotin-streptavidin system, the ddNTPs are normally biotin-labeled. After hybridization of biotin-labeled oligonucleotide probes with test oligonucleotides on a solid support, dye-coupled streptavidin are added and interacts with biotin. Color generated by streptavidin carried dyes is detected by scanning or imaging. While direct labeling of streptavidin is used sometimes for detection of biotin-labeled hybridized probes, signal amplification is achievable through enzyme based signal amplification. For example, streptavidin could be conjugated with antibodies. Signal could be amplified using antigen conjugated secondary biotin molecules. Dye labeled streptavidin is then used for signal detection. Alternatively, QuantumDot-streptavidin conjugates can be used for signal amplification. Horseradish Peroxidase coupled Streptavidin is another example, this time by chemiluminescent detection.

The oligonucleotide complements of the labeled probes are immobilized on a solid support. One kind of such support is beads. One way to detect the beads and the dye label is by flow cytometry. Details of flow cytometry detection of beads and associated dye label, and the use for differential gene expression analysis is disclosed in U.S. patent application Ser. No. 09/914,603, the disclosure of which is incorporated by reference in its entirety.

Another kind of solid support is that of a microscope slide or the like. The surface of a microscope slide can be a planar surface, or a gel polymer coated surface. Additionally, the surface may comprise a plurality of micro-features arranged in spatially discrete regions to produce a texture on the surface, wherein the textured surface provides an increase in surface area as compared to a non-textured surface. The attached oligonucleotides are arranged in a microarray format and the detection is by way of scanning or imaging of the microarray on the microscope slide.

The methods can be used to study gene expression of all genes within a genome, or alternatively to study gene expression of a sub-set of genes of interest. One gene specific oligonucleotide is used as a probe and a complement is used on the solid support. Therefore, for analysis of gene expression of the entire genome of *E. coli*, about 4,300 different gene specific non-cross hybridizing oligonucleotide pairs are needed. Likewise, the entire yeast genome is comprised of 6250 open reading frames (genes), and can be covered specifically by 6250 different gene specific noncross hybridizing oligonucleotide pairs. About 50,000 pairs are needed to cover every gene of the entire human genome. More oligonucleotide pairs are needed for analyzing alternative splicing of a genome, as more than one pair is needed for each gene.

The methods are preferably used for gene expression analysis of smaller, sub-sets of genes of interest. This could be any set of genes from an organism, or more likely a signature set of genes for a condition or trait. It is now known that there are signature sets of genes the expression of which are indicative of a human disease or condition, such as cancer, or metabolism of certain molecules and drugs. Measuring gene expression of these signature sets from an individual suspected of carrying a disease or condition leads to the diagnosis of the disease or condition, provided that the expression levels of said signature set of genes are compared to a predetermined expression signature related to a disease or condition. These methods are also useful for gene profiling of toxicogenomics studies and preclinical studies of model organisms, as well as animal diseases.

There are clear advantages of this new approach as compared to the other labeling protocols.

(1) Signal detected from the hybridized labeled probes is directly proportional to the gene expression level. This is because each labeled oligonucelotide probe carries only one label, as incorporated by the polymerase reaction. In contrast, probes generated from the earlier methods, including modified Eberwine method, are generally larger and contain varying number of labels. Little correlation between the detected signal and the true expression level can be established by use of the earlier methods. In the current approach, however, even when amplification is involved, probes generated still closely represent the gene expression level in the sample, due to linear rather than exponential amplification.

(2) Because first strand cDNA synthesis is optional, the current methods are ideally suited for the analysis of sample lacking a poly A tail. This is very useful in a number of situations. (i) Low quality samples, such as partially degraded RNA samples, as seen in many formalin fixed, paraffin embedded clinical samples, often does not contain the polyA tail. First strand synthesis of these samples using oligo dT primer can not be used to generate full length first strand cDNA, a necessary step for traditional labeling techniques. The use of an oligonucleotide probe as discussed in the current invention eliminates this problem and provides accurate expression information under these circumstances. (ii) The mRNA from bacterium does not contain a poly A tail, and therefore first strand cDNA can not be synthesized using a poly dT primer. In certain embodiments of the current invention, the probes hybridize directly to the mRNA template before the labeling reaction. This bypasses the requirement of a poly A tail for the mRNA, and is ideal for analyzing the expression of bacterial genes. (iii) Also because first strand cDNA synthesis is optional, the current methods are ideally suited when the probe sequence is at the 5' half of the gene.

(3) Since reverse transcription does not always complete to 5' end of the mRNA (due to enzyme falling off), sequence toward 5' of the gene is less well represented in the first strand cDNA pool. When the test sequence is chosen from near 5' end of a gene, expression analysis using probes generated from a cDNA template could not accurately reflect the true level of gene expression. Methods of the current invention, however, are not restricted as no reverse transcription is necessary.

(4) For the same reason, embodiments of the current invention are suited for detection of splice variant expressions, although many variants appear closer to the 5' end of the gene.

(5) The current invention is good for analyzing blood sample, or any sample that contains a high level of certain genes of no interest to the investigator. Analysis of blood sample is preferred in many clinical situations as it is considered less invasive. However, mRNA from blood contains a high level of (up to 70%) globin mRNA. For other methods such as modified Eberwine, the majority (up to 70%) of generated cDNA are from the globin source. This not only leads to a lot of wasted material during synthesis, it also reduces the amount of effective probe in the labeled sample, provided globin expression is of no relevance to the analysis. The current invention avoids these problems and obviates the need for subsequent globin depletion, by simply not to include globin gene specific probe in the primer extension/labeling step.

(6) With the current methods, it is possible to study expression of a specific set of genes from a larger set on a micro-array. For example, when one is interested in the expression level of only 200 genes on a 50,000 gene array, one can choose to use gene-specific oligonucleotide probes from those 200 genes. In this way, only the genes of interest are tested on the array, and other genes are not. This reduces chances of cross contamination of signals due to cross hybridization.

(7) The current methods greatly shorten the probe preparation work flow. As a comparison, the modified Eberwine method involves reverse transcription, second strand cDNA synthesis, aRNA generation, and biotin labeling. Not only does it require multiple enzymes, it also is a two-day procedure! The current probe preparation protocol only requires a single primer extension reaction, and can be easily finished within an hour of time.

(8) The current methods also shorten the hybridization time required to reach equilibrium. This is for three reasons. (1) The un-labeled oligonucleotide probes are not separated from the labeled ones before hybridization. Equal molar ratio oligonucleotide probes for each gene of interest are therefore present in the hybridization step, including some labeled and some un-labeled probes. Hybridization rate is not limited by the number of copy expressed for low level expressed genes. (2) Because hybridization is carried out with probes from genes of interest (not from all genes expressed), complexity of the hybridization reaction is greatly reduced. This results in reduced hybridization time for the reaction to reach completion. This is especially significant when used in detecting gene expression for a small set of genes, such as a signature for a certain disease or condition, which normally involves less than a few hundred genes. For these reasons, hybridization reaction is sped up significantly. (3) The oligonucleotide probes are selected for uniform hybridization at the design phase. This further speeds up hybridization of the probes and the test oligonucelotides.

(9) The current methods also result in efficient use of expensive dye-nucleotide analogs, as well as other reaction components. As discussed before, all labeled molecules serve as probes and none wasted, since no fragmentation of long cDNA probes are involved, compared to conventional methods which result in waste of sub-set of dye labeled fragments due to the lack of complementary sequence to the test oligonucleotides to be analyzed.

(10) There are other benefits as well. One advantage is the elimination of surface enzyme chemistry problems, since all that involved on surface is hybridization. Also, in some instances, there is no need to add all four ddNTP for the reaction. Use of one of the four is sufficient. Even then, the probes are generally not going to be more than 15 bases longer than the original oligonucleotide probe and are still good probes to use.

One embodiment of the invention includes first generating at least one oligonucleotide probe by a method of first algorithmically selecting a gene-specific target region sequence within each of at least one gene of interest; then synthesizing anti-sense oligonucleotide probes that complement each of the selected target regions; mixing the oligonucleotide probes with a source nucleic acid of interest to allow hybridization to occur; adding a labeled dideoxy nucleotide to the 3' end of hybridized oligonucleotide probes by polymerase reaction; and recovering said oligonucleotide probes. At the same time, providing test oligonucleotides on a solid support, the test oligonucleotides being complements in sequence to the probe oligonucleotides. Then hybridizing the labeled probe oligonucleotides with the test oligonucleotides, and detecting labels from the hybridized probe oligonucleotides on the solid support to determine the expression level of each of the at least one gene of interest.

In the above embodiment, the source nucleic acid of interest can be total RNA, mRNA or denatured cDNA. Ideally, the source nucleic acids are degraded or otherwise separated from the labeled oligonucleotide probes before the hybridization step. When the source nucleic acid is total RNA or mRNA, signal amplification is achievable easily by use of a thermostable polymerase with the ability to readily incorporate labeled ddNTP, such as a engineered or natural T7 DNA polymerase, DNA polymerase I, or a Reverse Transcriptase without a RNase activity. These enzymes exhibit very good reverse transcriptase activity for single nucleotide addition using RNA templates. Moreover, wild type Reverse Transcriptase with intact RNase H activity is only suitable for labeling without linear amplification because it will result in destruction of template RNA after first round of labeling. Cycling will result in linear increase of labeled probe products and the products generated will be directly proportional to the starting material copy number. This is one of the major advantages with this method.

Since extension is not needed on the arrayed oligonucleotide on slide or bead surface, either 3'-5' or 5'-3' mode of solid phase chemistry can be employed to anchor the complement oligonucleotides on slides. Thus the 3'-terminus of the arrayed oligonuleotides can be anchored. The orientation and exposure of the 3' or the 5' end of the test oligonucleotide is not critical.

FIG. 1 illustrates examples for gene expression analysis according to one embodiment of the invention. FIG. 1 (a) shows the embodiment as performed in a microarray-based format. FIG. 1 (b) shows the same embodiment, as performed in a bead-based format. The only difference is in the solid support being of different format. First, in a reaction tube, template RNA (mRNA or total RNA), a complementary probe (oligonucleotide probe), a suitable polymerase, and labelled ddNTP, such as Cy3 or Cy5-ddNTPs are mixed in solution. The oligonucleotide probe is extended by the polymerase for one base, and the labelled oligonucleotide probe carries the label from the labelled ddNTP. If additional labelled oligonucleotide probes are needed, the reaction is cycled repeatedly to allow linear amplification of labelled probes. Second, template RNA is removed. This could be achieved by RNA hydrolysis by alkali or RNase A, or affinity separation. Thirdly, the labelled oligonucleotide probesare used to hybridize the arrayed test oligonucleotides on slide or bead. The test oligonucleotid probes are in the same sense as the mRNAs. Lastly, the slides are scanned or imaged to detect the label and record the intensity of the signal. Any positive signal detected from a location implies expression of the particular gene represented by the spotted test oligonucleotide, and intensity of signal is a direct indication of the level of gene expression. This method eliminates surface enzyme chemistry problems. Limitation with DNA hybridization kinetics on slide/bead is minimized as well. There is also no need for fragmentation of probes.

Figure 2A:
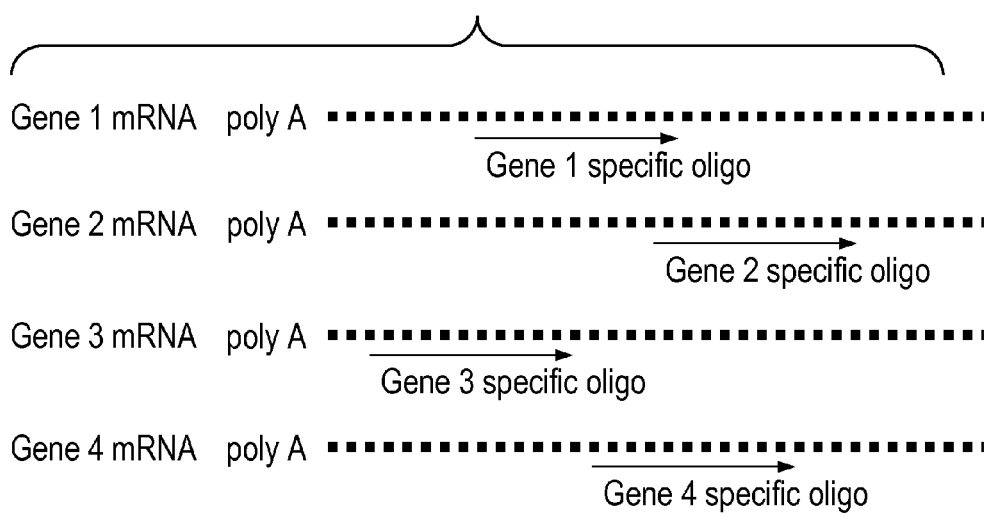
FIG. 2A is a schematic diagram showing the gene specific oligo hybridized to mRNA of each gene, prior to the labeling reaction.
Figure 2B:
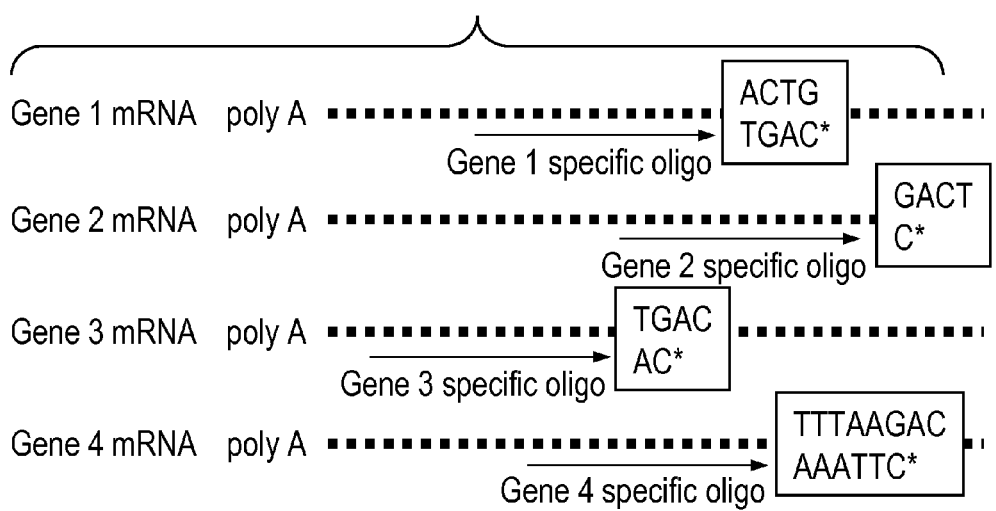
FIG. 2B is the schematic diagram after the labeling reaction.

FIG. 2 illustrates an alternative probe labeling scheme for gene expression analysis according to the embodiments of this invention. Labeling of the probe oligonucleotide is performed with a labeled ddCTP and un-labeled dATP, dGTP and dTTP. Labeling of the probe oligonucleotide occurs when the C is incorporated. FIG. 2A shows mRNA from four different genes at a 3'-5' orientation, with a gene specific oligonucleotide probe shown underneath each of the gene. FIG. 2B shows the result of primer extension, including repeated rounds of primer extension reaction (cycling). As shown in the figure, extension is terminated at the incorporation of the labeled ddCTP. Depending upon the sequence context, in some genes the placement of the selected oligonucleotide probe may result in the probe length of n+1, n+2 and so forth, but unlikely to be higher than n+15 for a vast majority of probes generated. Even so, these are ideal length probes for test targets on slides/beads.

In an alternative embodiment, a sense oligonucleotide probe is used, as opposed to an anti-sense oligonucleotide probe. In this embodiment, first strand cDNA is generated from an RNA source, and first strand cDNA is mixed with the oligonucleotide probes to allow hybridization and polymerase extension of the oligonucleotide probes with the cDNA. The test oligonucleotides on a solid support are complements in sequence to the probe oligonucleotides, and therefore anti-sense to the gene sequence.

In principle, one could run two different labeling processes on two different samples with two different labels for differential gene expression analysis using these methods. Comparative analysis of more than two samples is also achievable, in as much as the labels used are distinct among each other. If differential gene expression is desired, a parallel reaction using sample nucleic acid from different cell types or different treatments or test and controls are generated using the same principle except with different dye or hapten-labeled nucleotides (e.g. Cy3 and Cy5-ddNTP, or Cy3 and Cy5-ddCTP plus dATP, dTTP, dGTP).

The following describes the basic steps involved for a comparative expression analysis of two source nucleic acids of interest. Analysis of multiple samples can be achieved by either including additional samples in the same analysis, or comparing each sample to a single standard sample, one at a time. These comparisons are useful for generating diagnostic profiles or signatures for a certain condition or disease. Many times the method includes one source nucleic acid from a normal control, and the other source nucleic acids from a disease, experimental treatment or condition. Gene expression signatures associated with a disease or condition are obtained by repeated comparative gene expression analysis of many samples, and followed by algorithmic analysis of the relative expression levels for each gene.

As an example, basic steps involved for a comparative expression analysis of two source nucleic acids of interest include first labeling the oligonucleotide probes with different labels. For one sample, limited primer extension/termination followed by cycling, in the presence of dATP, dTTP, dGTP, Cy3-ddCTP and a thermostable reverse transcriptase (or any polymerase having RNA template dependent DNA synthesis activity) lead to the generation of Cy3 labeled oligonucleotide probes from an RNA template. For the second sample, Cy5 labeled oligonucleotide probes are generated with a similar process. Although ddCTP is used in the example, any one of the four nucleotides could serve as terminator, although the dNTP version of that terminator nucleotide has to be excluded in the mixture containing the other three dNTPs. Dye or hapten-labeled ddNTP could also be used. The polymerase used could be TtsFY, with optional addition of glycerol and other stabilizers for cycling. If RNA degradation is feared at high temperature, an alternate method, full-length 1st strand cDNA synthesis using oligo dT primers and Superscript II is first accomplished. Using that template strand a limited primer extension/terminator reaction and cycling using the above approach with TSI or any thermostable FY DNA pol I with cycling can then be undertaken to generate additional labeled oligonucleotide probes.

The Cy3 and Cy5 labeled oligonucleotide probes generated above are then mixed together and used to hybridize to the test partners on oligonucleotide arrays or beads. The probes should only bind to their complementary test oligonucleotides on the array or bead. Once hybridization is complete, the Cy3 and Cy5 signals are detected and quantified to determine the expression level of each gene from the two samples.

The major advantages of this strategy are that probes generated are bright, short, and closely represent the gene expression level in the sample due to linear rather than exponential amplification. This strategy also results in maximal and efficient use of expensive dye-nucleotide analogs. All labeled molecules serve as probes and none wasted, unlike the fragmentation of long cDNA or RNA probes generated by conventional methods which results in waste of sub-set of fragments due to the lack of complementary sequence on the solid support. It is also not necessary to separate the un-labeled oligonucleotide probes from the labeled ones before hybridization. Probes entering the hybridization reaction are at the same concentration, although the amount of labeled probes varies due to differences in gene expression level. This increases the efficiency and speed of hybridization, and offers an added form of normalization, as probes from each gene are at the same concentration during hybridization.

Also provided are kits for gene expression analysis. One such kit comprises gene-specific oligonucleotide probes for each gene of interest, and test oligonucleotides on a solid support, such as a microarray slide or beads. Such kits can also include a labeled dideoxy nucleotide, and a DNA polymerase I or a reverse transcriptase. The gene expression analysis method is useful for the diagnosis of human disease or condition. It is therefore also provided a kit for every human disease or condition that has an association with an expression profile (signature).

If it is desired to remove the un-labeled probes post labeling, alpha phosphorothio Cy3 or Cy5-ddCTP could be used to replace Cy3, Cy5-ddCTP for the labeling reaction. This approach allows for selective removal of un-labeled probes post labeling by treatment by some simple means such as treatment with Exo I. It is known that Exo I can digest away un-labeled probes while leaving intact extended probes, owing to the protection from phosphorothioate bond of the terminal nucleotide. This allows for elimination of potential target site saturation for competing hybridization from labeled vs un-labeled probes. It is also useful during comparative hybridization, as the concentration of un-labeled probes is higher due to the pooling of probes from more than one labeling reaction.

Having described the particular, desired embodiments of the invention herein, it should be appreciated that modifications may be made therethrough without departing from the contemplated scope of the invention. The true scope of the invention is set forth in the claims appended hereto.

What is claimed is:

1. A method for human gene expression analysis, comprising:
   (i) generating oligonucleotide probes by a method comprising:
      (a) selecting a gene-specific target region sequence for each gene of interest for a signature set of genes the expression of which is indicative of a disease or condition;
      (b) synthesizing anti-sense oligonucleotide probes that complement each of said selected target sequence for each of said at least one known gene of interest;
      (c) mixing said oligonucleotide probes with isolated total RNA or mRNA to allow hybridization to occur;
      (d) adding a labeled dideoxy nucleotide to the 3' end of hybridized oligonucleotide probes by polymerase reaction; and
      (e) recovering said oligonucleotide probes by removal or hydrolysis of said RNA;
   (ii) providing test oligonucleotides on a solid support, said test oligonucleotides being complements in sequence to the probe oligonucleotides, wherein said solid support is a microarray slide, and wherein said test oligonucleotides are arranged to form a microarray;
   (iii) hybridizing said probe oligonucleotides generated from step (i) above with said test oligonucleotides; and
   (iv) detecting and measuring signal intensity of said labels from said hybridized probe oligonucleotides on said solid support to determine the expression level of each of said at least one gene of interest wherein said signal intensity is proportional to the expression level of each gene.

2. A method for human gene expression analysis, comprising:
   generating oligonucleotide probes by a method comprising:
      (a) selecting a gene-specific target region sequence for each gene of interest for a signature set of genes the expression of which is indicative of a disease or condition;
      (b) synthesizing a sense oligonucleotide probe identical in sequence to said target region of each of at least one gene of interest;
      (c) generating first strand cDNA from an isolated RNA source;
      (d) mixing said oligonucleotide probes with said cDNA to allow hybridization of said oligonucleotide probes with complement strands of cDNA;
      (e) adding a labeled dideoxy nucleotide to the 3' end of hybridized oligonucleotide probes by polymerase reaction; and
      (f) recovering said oligonucleotide probes by removal or hydrolysis of said source RNA;
   (ii) providing test oligonucleotides on a solid support, said test oligonucleotides being complements in sequence to the probe oligonucleotides, wherein said solid support is a microarray slide, and wherein said test oligonucleotides are arranged to form a microarray;
   (iii) hybridizing said probe oligonucleotides generated from step (i) above with said test oligonucleotides; and
   (iv) detecting and measuring signal intensity of said labels from said hybridized probe oligonucleotides on solid support to determine the expression level of each of said at least one gene of interest wherein said signal intensity is proportional to the expression level of each gene.

3. The method for gene expression analysis of claim 1 or 2, wherein said target region sequences are from about 10 to about 100 nucleotides in length.

4. The method for gene expression analysis of claim 1 or 2, wherein said target region sequences are from about 20 to about 60 nucleotides in length.

5. The method for gene expression analysis of claim 1 or 2, wherein said target region sequences are from about 20 to about 30 nucleotides in length.

6. The method for gene expression analysis of claim 2, wherein said source RNA is selected from the group consisting of total RNA and mRNA.

7. The method for gene expression analysis of claim 1 or 6, wherein said total RNA or said mRNA is degraded during or after polymerase reaction.

8. The method for gene expression analysis of claim 1 or 2, wherein more oligonucleotide probes are produced by repeated denature, hybridization and polymerase reaction.

9. The method for gene expression analysis of claim 1 or 2, wherein said adding step is performed in the presence of all four labeled ddNTP.

10. The method for gene expression analysis of claim 1 or 2, wherein said adding step is performed in the presence of a single labeled dideoxy nucleotide and three non-labeled deoxynucleotides.

11. The method for gene expression analysis of claim 1 or 2, wherein said adding step is performed in the presence of labeled ddCTP and non-labeled dATP, dGTP and dTTP.

12. The method for gene expression analysis of claim 1 or 2, wherein said labeled dideoxy nucleotide contains a hapten label.

13. The method for gene expression analysis of claim 1 or 2, wherein said labeled dideoxy nucleotide contains a fluorescent dye label.

14. The method for gene expression analysis of claim 1 or 2, wherein said labeled dideoxy nucleotide contains a dye label selected from the group consisting of Cyanine, Infra Red, and Rhodamine dyes.

15. The method for gene expression analysis of claim 1 or 2, wherein said detecting step further includes a signal amplification step using streptavidin-conjugates.

16. The method for gene expression analysis of claim 12, wherein said hapten label is a biotin label.

17. A method for human comparative gene expression analysis, comprising:
   (i) generating oligonucleotide probes by a method comprising:
      (a) selecting a gene-specific target region sequence for each gene of interest for a signature set of genes the expression of which is indicative of a disease or condition; and
      (b) synthesizing anti-sense oligonucleotide probes that complement each of said selected target regions;
   (ii) labeling said oligonucleotide probes with distinctive dyes for each of the isolated source total RNA or mRNA to be analyzed, by a method comprising:
      (a) mixing a portion of said oligonucleotide probes with one of said source total RNA or mRNA to allow hybridization to occur;
      (b) adding a labeled dideoxy nucleotide to the 3' end of hybridized oligonucleotide probes by polymerase reaction;
      (c) recovering said oligonucleotide probes by removal or hydrolysis of said source RNA;

(d) repeating steps (ii) (a) through (ii) (c) with a distinctive label for each additional source total RNA or mRNA of interest; and (e) combining said portions of oligonucleotide probes;

(iii) providing test oligonucleotides on a solid support, said test oligonucleotides being complements in sequence to the probe oligonucleotides, wherein said solid support is a microarray slide, and wherein said test oligonucleotides are arranged to form a microarray;

(iv) hybridizing said labeled probe oligonucleotides generated from step (ii) above with said test oligonucleotides on said solid support;

(v) detecting and measuring signal intensity of each of said distinctive labels from said hybridized probe oligonucleotides wherein said signal intensity is proportional to the expression level of each gene; and (vi) determining the relative expression level for each gene from total RNA or mRNA of interest.

18. A method for human comparative gene expression analysis, comprising:

(i) generating oligonucleotide probes by a method comprising:

(a) selecting a gene-specific target region sequence for each gene of interest for a signature set of genes the expression of which is indicative of a disease or condition; and (b) synthesizing a sense oligonucleotide probe identical in sequence to said target region sequence of each of at least one gene of interest;

(ii) labeling said oligonucleotide probes with distinctive dyes for each of the isolated source RNA to be analyzed, by a method comprising:

(a) generating first strand cDNA from one of said source RNA;

(b) mixing a portion of said oligonucleotide probes with said cDNA to allow hybridization of said oligonucleotide probes with said cDNA;

(c) adding a labeled dideoxy nucleotide to the 3' end of hybridized oligonucleotide probes by polymerase reaction;

(d) recovering said oligonucleotide probes by removal or hydrolysis of said source RNA;

(e) repeating steps (ii)(a) through (ii)(e) with a distinctive label for each additional source RNA of interest; and (f) combining said portions of oligonucleotide probes;

(iii) providing test oligonucleotides on a solid support, said test oligonucleotides being complements in sequence to the probe oligonucleotides, wherein said solid support is a microarray slide, and wherein said test oligonucleotides are arranged to form a microarray;

(iv) hybridizing said probe oligonucleotides generated from step (ii) above with said test oligonucleotides on solid support;

(v) detecting and measuring signal intensity of each of said distinctive labels from said hybridized probe oligonucleotides on solid support wherein said signal intensity is proportional to the expression level of each gene; and (vi) determining the relative expression level for each gene from source RNA of interest.

19. The method for comparative gene expression analysis of claim 17 or 18, wherein one source RNA is from a normal control, and the other source RNA are from said disease or condition.

* * * * *